United States Patent [19]

Tsao et al.

[11] Patent Number: 5,256,420
[45] Date of Patent: Oct. 26, 1993

[54] METHOD OF IMPARTING ANTIMICROBIAL ACITIVITY TO AN OPHTHALMIC COMPOSITION

[75] Inventors: Fu-Pao Tsao, Lawrenceville; Paul C. Nicolson, Dunwoody; Susan A. Littlefield, Duluth, all of Ga.

[73] Assignee: Ciba-Geigy Corporation, Ardsley, N.Y.

[21] Appl. No.: 812,780

[22] Filed: Dec. 23, 1991

[51] Int. Cl.5 ............ A61K 31/14; A61K 31/74
[52] U.S. Cl. .................. 424/427; 424/78.04; 424/429; 514/642; 514/912
[58] Field of Search ............ 424/427, 78.04, 429; 514/642, 912

[56] References Cited

U.S. PATENT DOCUMENTS 4,407,791 10/1983 Stark .................. 424/78.04
4,525,346 6/1985 Stark .................. 424/78.04

Primary Examiner—Thurman K. Page
Assistant Examiner—James M. Spear
Attorney, Agent, or Firm—Edward McC. Roberts; William G. Hervey

[57] ABSTRACT

A method of imparting antimicrobial activity to an ophthalmic composition includes the step of adding a polyquaternary ammonium salt to the composition. The method may be employed, for example, for disinfecting a contact lens or preserving a solution, ointment or suspension.

12 Claims, No Drawings

METHOD OF IMPARTING ANTIMICROBIAL ACITIVITY TO AN OPHTHALMIC COMPOSITION

BACKGROUND OF THE INVENTION

The present invention relates to a method of imparting antimicrobial activity to an ophthalmic composition. More particularly, it relates to the use of a particular polymeric quaternary ammonium compound to improve disinfectant and preservative qualities in compositions which come into contact with the eye or with ophthalmic devices, such as contact lenses.

The sensitive nature of the ocular environment mandates antimicrobial methods which provide high bactericidal efficacy coupled with low cytotoxicity. A number of preserving and disinfecting methods are known in the contact lens art. Typically, these methods employ either sorbic acid, thimerosal, chlorhexidine or a conventional quaternary germicide such as benzalkonium chloride. However, these antimicrobial compounds have drawbacks that tend to restrict their use. For example, sorbic acid characteristically contains formaldehyde residues; and thimerosal, chlorhexidine and BAK may cause eye irritation.

U.S. Pat. Nos. 4,525,346 and 4,407,791 to Stark relates to antimicrobial ophthalmic compositions containing the quaternary ammonium compound "1-tris(2-hydroxyethyl)ammonium-2-butenyl-4-poly[1-dimethyl ammonium-2-butenyl]-w-tris(2-hydroxyethyl) ammonium." This compound, however, is unstable in the presence of hydrogen peroxide, which is used in a number of contact lens disinfecting and preserving methods. It is also subject to improvement in bactericidal efficacy, particularly in instances involving Serratia marcescens.

Therefore, there exists a need for an improved method of imparting antimicrobial activity to ophthalmic compositions.

There exists a further need for such a method which utilizes a compound which has low cytotoxicity and high bactericidal efficacy.

There exists a further need for such a method which can be employed regardless of the presence of hydrogen peroxide.

SUMMARY OF THE INVENTION

The object of the present invention is to provide a method for imparting antimicrobial activity to an ophthalmic composition which can be successfully employed regardless of the presence of hydrogen peroxide. The method includes the step of adding a previously known polymeric quaternary ammonium salt, described in detail below, the composition to provide low cytotoxicity and high bactericidal efficacy, particularly in instances involving Serratia marcescens. The method may be used for disinfecting a contact lens or preserving a solution, ointment or suspension.

DETAILED DESCRIPTION OF THE INVENTION

The present invention relates to a method of imparting antimicrobial activity to an ophthalmic composition by adding to the composition a previously known polymeric quaternary ammonium salt compound. Surprisingly, it has been found that employing the method of the invention provides a composition that is stable in the presence of hydrogen peroxide, which is present in a number of contact lens disinfection and preservative systems and which is known to cause yellowing of lenses in other types of quaternary ammonium salt-based compositions. The method is particularly advantageous when used with rigid gas permeable lenses, such as those made of polymethyl methacrylate, and in other instances where the compound is not absorbed into the matrix of the lens.

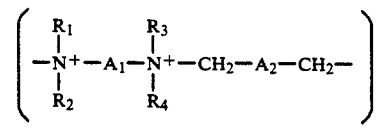

in which $R_1$, $R_2$, $R_3$ and $R_4$ are identical or different from one another and are optionally substituted alkyl, cycloalkyl with at most 20 carbon atoms, aryl, aralkyl, or a substituted heterocyclic ring with 3 to 6 ring members, $A_1$ is $-(CH_2)_m-$, in which m is a number from 1 to 20 which is optionally interrupted by at least one

grouping or substituted by at least one hydroxyl, halogen, nitrile, alkyl, hydroxyalkyl, alkoxy, carboxyl, carbalkoxy, a substituted aryl or aralkyl radical, polyoxyalkylene or a radical of the formula

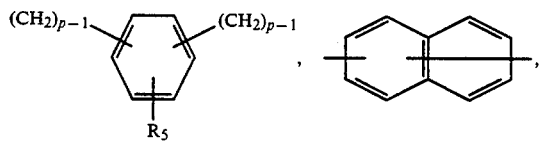

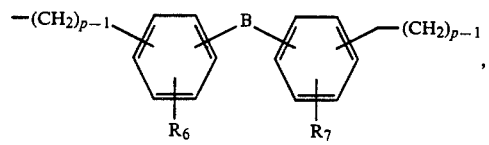

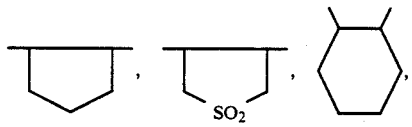

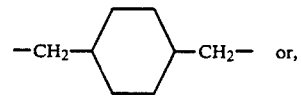

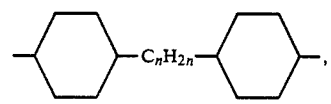

or, together with the nitrogen atoms and at least one of the substituents bonded to each nitrogen atom, is a radical of the formula

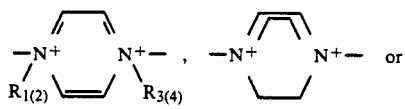

$R_6$ and $R_7$ are hydrogen, alkyl, hydroxyalkyl or halogenoalkyl with 1 to 4 carbon atoms, hydroxyl, halogen, carboxyl, carbalkoxy or phenyl;

B is a direct bond, —O—, —SO$_2$—,

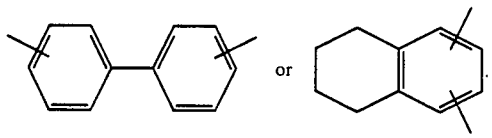

or optionally substituted alkylene;
n is a number from 1 to 6;
p is a number from 1 to 3; and
$A_2$ is a radical having the formulae

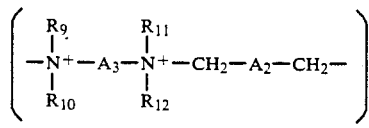

In one embodiment of the invention, the structure of the cationic units correspond to the formula

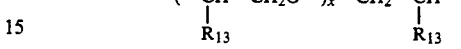

and $R_9$, $R_{10}$, $R_{11}$ and $R_{12}$ are alkenyl with 2 to 20 carbon atoms, hydroxyl, cycloalkyl with 5 to 6 carbon atoms; alkyl, hydroxyalkyl, cyanoalkyl, alkoxyalkyl, alkylcarbonalkyl with 1 to 10 carbon atoms, arylcarbonylalkyl, alkylsulphonylalkyl and arylsulphonylalkyl each with 1 to 4 carbon atoms in the alkyl part; alkylcarboxylic acid with 1 to 4 carbon atoms in the alkyl part; carbalkoxyalkyl and di-(carbaloxy)-alkyl each with 1 to 4 carbon atoms in the alkoxy part and the alkyl part; carboxamidoalkyl which has 1 to 10 carbon atoms in the alkyl part and is optionally N-substituted by lower alkyl or aryl; phenyl, benzyl, optionally substituted by hydroxyl, cyano, halogen or carboxyl; alkyl, hydroxyalkyl, cyanoalkyl, alkoxy with 1 to 4 carbon atoms; alkoxyalkyl, carbalkoxyalkyl and di-(carbalkoxy)-alkyl each with 1 to 4 carbon atoms in the alkyl part and the alkoxy part; alkylcarboxylic acid with 1 to 4 carbon atoms in the alkyl part; carboxamidoalkyl which has 1 to 4 carbon atoms in the alkyl part and is optionally N-substituted by lower alkyl; and ($R_9$ and $R_{10}$) and ($R_{11}$ and $R_{12}$), together with the nitrogen atom to which they are bonded, form an optionally substituted heterocyclic ring with 5 to 6 ring members;

and in which $A_3$ is —(CH$_2$)$_m$—, where m is a number from 1 to 20, which is optionally interrupted by at least one

grouping or substituted by at least one hydroxyl, chlorine, nitrile, alkyl, alkoxy or hydroxyyalkyl with 1 to 4 carbon atoms, carboxyl or carbalkoxy with 1 to 4 carbon atoms in the alkoxy radical or by optionally substituted phenyl or benzyl radicals;

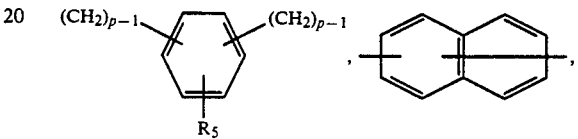

or a radical having the formula

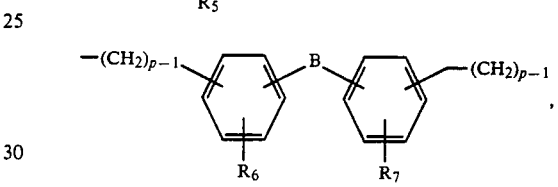

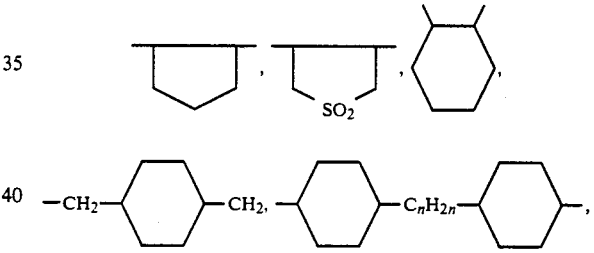

or, together with the nitrogen atoms and at least one of the substituents which are bonded to each of the nitrogen atoms, is a radical of the formula

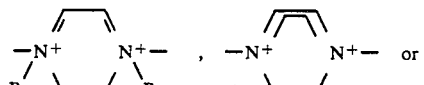

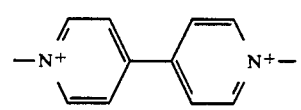

and $R_{13}$ is hydrogen or methyl and x is at least 1.

In another aspect of the invention, the cationic units may correspond to the formula

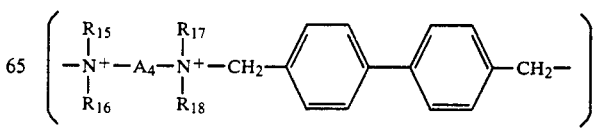

in which $R_{15}$, $R_{16}$, $R_{17}$ and $R_{18}$ are alkyl, hydroxyalkyl, alkoxyalkyl, cyanoalkyl with 1 to 4 carbon atoms, cyclopentyl, cyclohexyl, alkenyl with 2 to 4 atoms, $CH_3COCH_2-$, $HOOCCH_2-$, $CH_3OOCCH_2-$, $H_5C_2OOCCH_2-$, $(CH_3OOC)_2CH-$, $H_2NCOCH_2-$,

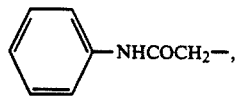

phenyl or benzyl, optionally substituted by hydroxyl, cyano, fluorine, chlorine, bromide, alkyl, hydroxyalkyl, cyanoalkyl, alkoxy with 1 or 2 carbon atoms, alkoxyalkyl, carboxyalkyl or di-(carboxyalkyl), each with 1 or 2 carbon atoms in the alkyl part which has 1 or 2 carbon atoms in the alkyl part and is optionally N-substituted by lower alkyl; or ($R_{15}$ and $R_{16}$) and/or ($R_{17}$ and $R_{18}$), together with the nitrogen atom to which they are bonded, form a heterocyclic ring of the formula

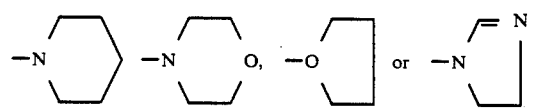

and $A_4$ is $-(CH_2)-_{m_1}$, in which $m_1$ is a number from 1 to 12,

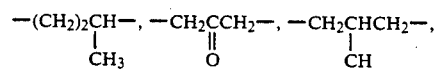

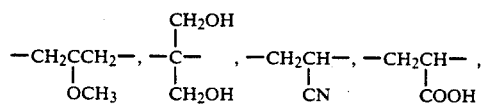

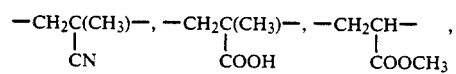

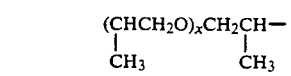

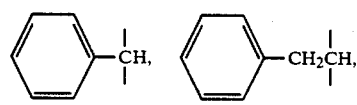

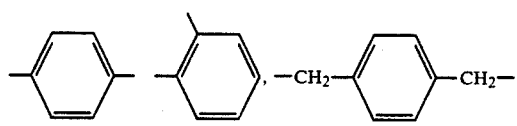

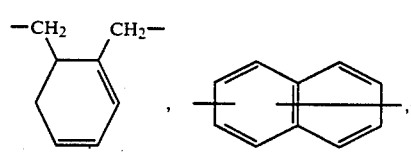

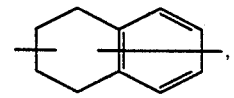

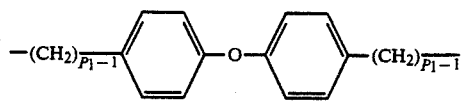

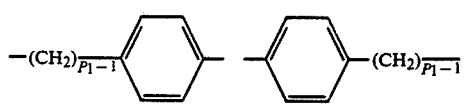

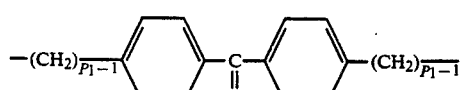

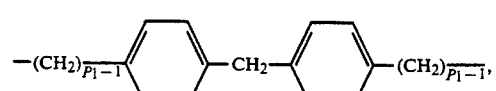

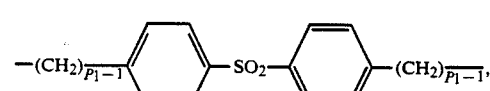

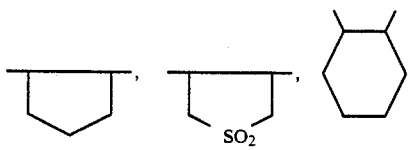

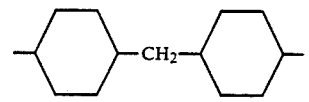

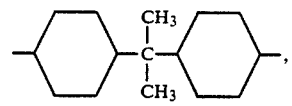

in which x is at least 1 and $P_1$ is 1 or 2, or together with the nitrogen atoms and at least one of the substituents bonded to each nitrogen atom, is a radical of the formula

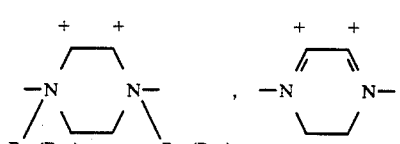

or

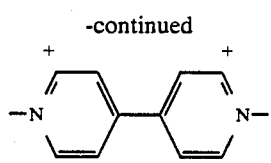

The preferred polyquaternary ammonium compound for use in the present method has the formula wherein the recurring units are

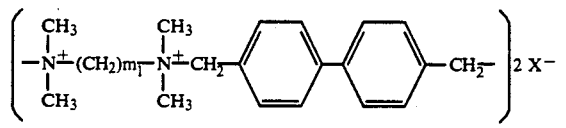

in which $m_1$ is 1 to 12 and X is halogen. An example of the above-described preferred compound is available under the tradename Polyquat D-17-1242 from CIBA Geigy Corporation, Ardsley, N.Y., and contains recurring units corresponding to the formula

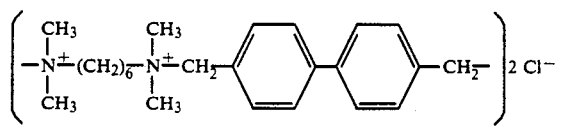

The method of the present invention may be employed, by way of example, for disinfecting contact lenses or other ophthalmic devices, as well as for preserving contact lens compositions such as cleaning or wetting solutions. In addition, the disinfectant and preservative qualities of the polyquaternary compound may be combined in a single product. The quaternary ammonium compound may be used at concentrations ranging from about 0.00001% to 3%, taking ocular irritation into consideration. The preferred concentration of the compound in a disinfecting solution is from about 0.001% to about 0.005% by weight/volume of the composition, and the preferred concentration of the compound as a preservative is about 0.0005% by weight/volume of the composition.

For illustration purposes, Example I below is an aqueous formulation of a solution incorporating the present method. The formulation may be used, for example, as a combined contact lens cleaning/disinfecting solution, with the only additional consideration being the presence of a fungicide to meet current U.S. Food and Drug Administration requirements for a disinfectant. Also, the solution can be used in the presence of hydrogen peroxide with no harmful effect to the lens.

| EXAMPLE I | |
|---|---|
| Polyquaternary compound D-17-1242 (20% solid from CIBA-Geigy Corp.) | 0.004% |
| Citric acid | 0.1% |
| Pluronic P127 | 0.05% |
| Hydrogen peroxide | 0.005% |
| Dequest 2060 | 0.006% |
| Sodium chloride | 0.61% |
| Sodium tetraborate · 10 H$_2$O | 0.005% |
| Boric acid | 0.5% |
| Deionized H$_2$O q.s. | 100 ml |
| q.s. pH | 7.0 |

It has been found that the present method provides good bactericidal efficacy (as demonstrated by the data below) coupled with low cytotoxicity. The following data indicates the results of antimicrobial solutions (Samples I and II, below), incorporating the method of the present invention, that were screened using $10^8$ Serratia marcescens ATCC 14041. The samples were taken 1 hour after 0.1 ml inoculations of each solution.

SAMPLE I

Dissolve from 0.0001 to 0.004 gram (0.0001%, 0.0005%, 0.0010%, 0.0020%, 0.0040%) of Polyquat D-17-1242 (20% solid as set forth above, available from CIBA-Geigy Corporation, Ardsley, N.Y.), 0.1 gram of DEAE-Dextran, 0.1 gram citric acid, 0.61 gram sodium chloride, 0.005 gram sodium tetraborate 10 H$_2$O, 0.5 gram boric acid, and 0.0225 gram sodium perborate in 80 ml of deionized water. Adjust the pH of the solution to 7.0 by dilute HCl or dilute NaOH. Add the balance of deionized water up to the 100 ml mark. The antimicrobial test results are listed below in Table I.

SAMPLE II

Dissolve 0.0050 gram of Polyquat D-17-1242 (20% solid, as in Example 1 above), 0.61 gram sodium chloride, 0.005 gram sodium tetraborate 10 H$_2$O, and 0.5 gram boric acid in 80 ml of deionized water. Adjust the PH to 7.0 by dilute HCl or dilute NaOH and add deionized water up to the 100 ml mark.

The following are the results of the solutions of SAMPLES I and II above which were challenged with Serratia marcescens ATCC 14041. The Samples were plated after one hour following a 0.1 ml inoculation of the bacteria.

TABLE I

| Solution | Results (cfu/ml) |
|---|---|
| PBS Control | 5.6 × 10$^5$ |
| Example 1 | |
| 0.0001% | 2.2 × 10$^5$ |
| 0.0005% | 2.1 × 10$^5$ |
| 0.0010% | 2.3 × 10$^5$ |
| 0.0020% | 0 |
| 0.0040% | 0 |
| Example 2 | 0 |

What is claimed is:

1. A method of imparting antimicrobial activity to an ophthalmic composition, in the presence of hydrogen peroxide comprising adding to the composition a quaternary ammonium salt in which the cationic units correspond to the formula

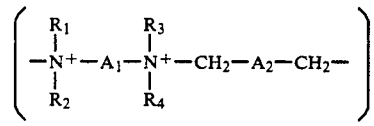

in which
 $R_1$ $R_2$, $R_3$ and $R_4$ are identical or different from one another and are selected from the group consisting of optionally substituted alkyl, cycloalkyl with at most 20 carbon atoms, aryl, aralkyl, and a substituted heterocyclic ring with 3 to 6 ring members,
 $A_1$ is $-(CH_2)_m-$, in which m is a number from 1 to 20 which is optionally interrupted by at least one

grouping or substituted by at least one of hydroxyl, halogen, nitrile, alkyl, hydroxyalkyl, alkoxy, carboxyl, carbalkoxy, a substituted aryl or aralkyl radical, polyoxyalkylene or a radical of the formula

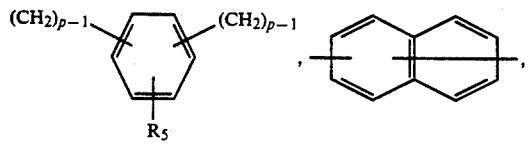

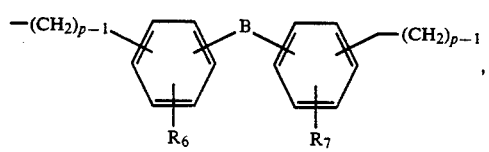

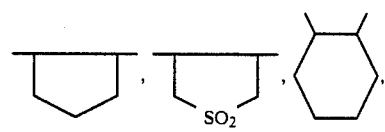

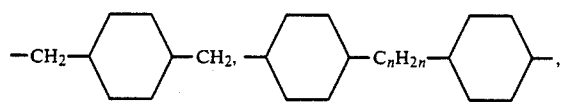

or, together with the nitrogen atoms and at least one of the substituents bonded to each nitrogen atom, is a radical of the formula

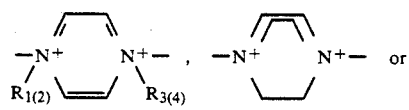

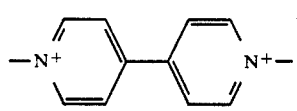

$R_6$ and $R_7$ are selected from the group consisting of hydrogen, alkyl, hydroxyalkyl or halogenoalkyl with 1 to 4 carbon atoms, hydroxyl, halogen, carboxyl, carbalkoxy and phenyl;
B is selected from the group consisting of a direct bond, —O—, —SO$_2$—,

and optionally substituted alkylene;
n is a number from 1 to 6;
p is a number from 1 to 3; and
$A_2$ is a radical having the formula

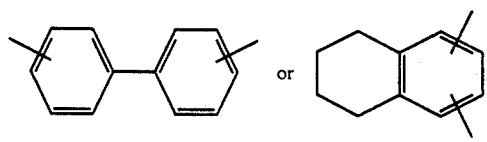

2. The method of claim 1, wherein the cationic units correspond to the formula $$\left( \begin{array}{c} R_9 \\ | \\ -N^+-A_3-N^+-CH_2-A_2-CH_2- \\ | \\ R_{10} \end{array} \begin{array}{c} R_{11} \\ | \\ | \\ R_{12} \end{array} \right)$$

in which
$R_9$, $R_{10}$, $R_{11}$ and $R_{12}$ are identical or different from one another and are selected from the group consisting of hydroxyl; cycloalkyl with 5 to 6 carbon atoms; alkyl, hydroxyalkyl, cyanoalkyl, alkoxyalkyl, alkylcarbonalkyl with 1 to 10 carbon atoms; arylcarbonylalkyl, alkylsulphonylalkyl and arylsulphonylalkyl each with 1 to 4 carbon atoms in the alkyl part; alkylcarboxylic acid with 1 to 4 carbon atoms in the alkyl part; carbalkoxyalkyl and di-(carbaloxy)-alkyl each with 1 to 4 carbon atoms in the alkoxy part and the alkyl part; carboxamidoalkyl which has 1 to 10 carbon atoms in the alkyl part and is optionally N-substituted by lower alkyl or aryl; phenyl, benzyl, optionally substituted by hydroxyl, cyano, halogen or carboxyl; alkyl, hydroxyalkyl, cyanoalkyl, and alkoxy with 1 to 4 carbon atoms; alkoxyalkyl, carbalkoxyalkyl and di-(carbalkoxy)-alkyl each with 1 to 4 carbon atoms in the alkyl part and the alkoxy part; alkylcarboxylic acid with 1 to 4 carbon atoms in the alkyl part; carboxamidoalkyl which has 1 to 4 carbon atoms in the alkyl part and is optionally N-substituted by lower alkyl; and ($R_9$ and $R_{10}$) and ($R_{11}$ and $R_{12}$), together with the nitrogen atom to which they are bonded, form an optionally substituted heterocyclic ring 5 or 6 ring members;
$A_3$ is —(CH$_2$)$_m$—, in which m is a number from 1 to 20, which is optionally interrupted by at least one

grouping or substituted by at least one hydroxyl, chlorine, nitrile, alkyl, alkoxy or hydroxyyalkyl with 1 to 4 carbon atoms, carboxyl or carbalkoxy with 1 to 4 carbon atoms in the alkoxy radical or by optionally substituted phenyl or benzyl radicals;

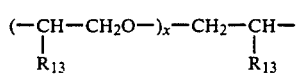

a radical having the formulae

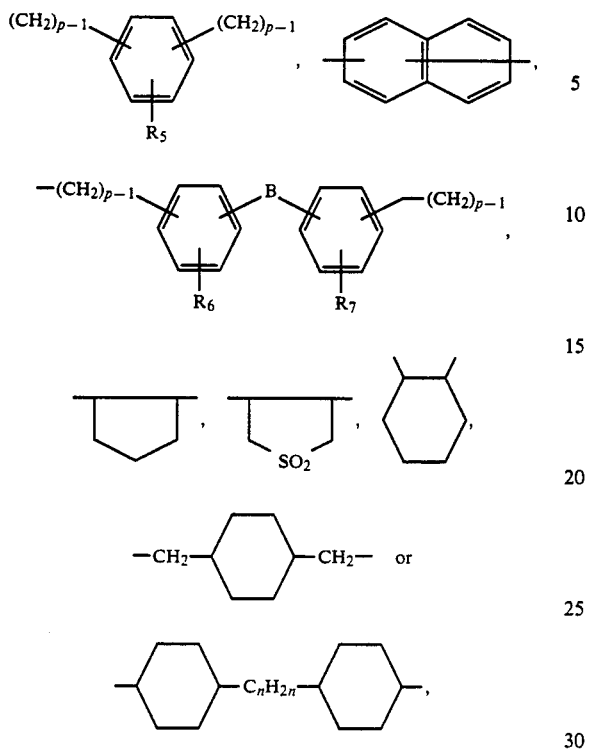

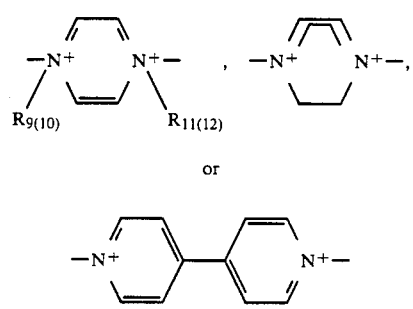

or, together with the nitrogen atoms and at least one of the substituents which are bonded to each of the nitrogen atoms, is a radical of the formulae

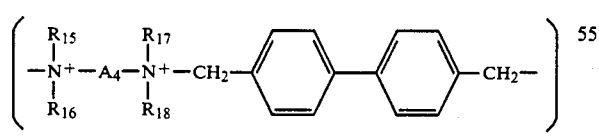

and $R_{13}$ is hydrogen or methyl and x is at least 1.

3. The method of claim 1, wherein the cationic units correspond to the formula $$\left( \begin{array}{c} R_{15} \\ -N^+-A_4-N^+-CH_2-\phantom{xx}\phantom{xx}-CH_2- \\ R_{16} \end{array} \begin{array}{c} R_{17} \\ \\ R_{18} \end{array} \right)$$

in which $R_{15}$, $R_{16}$, $R_{17}$ and $R_{18}$ are identical or different from one another and are selected from the group consisting of alkyl, hydroxyalkyl, alkoxyalkyl, cyanoalkyl with 1 to 4 carbon atoms, cyclopentyl, cyclohexyl, alkenyl with 2 to 4 atoms, $CH_3COCH_2-$, $HOOCCH_2-$, $CH_3OOCCH_2-$, $H_5C_2OOCCH_2-$, $(CH_3OOC)_2CH-$, $H_2NCOCH_2-$,

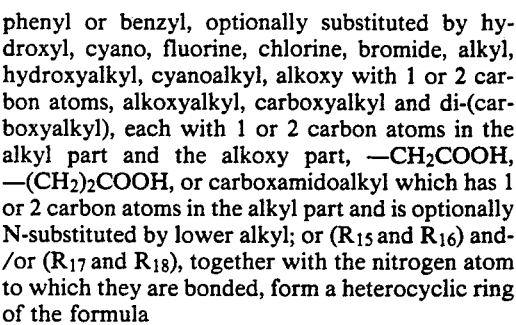

phenyl or benzyl, optionally substituted by hydroxyl, cyano, fluorine, chlorine, bromide, alkyl, hydroxyalkyl, cyanoalkyl, alkoxy with 1 or 2 carbon atoms, alkoxyalkyl, carboxyalkyl and di-(carboxyalkyl), each with 1 or 2 carbon atoms in the alkyl part and the alkoxy part, $-CH_2COOH$, $-(CH_2)_2COOH$, or carboxamidoalkyl which has 1 or 2 carbon atoms in the alkyl part and is optionally N-substituted by lower alkyl; or ($R_{15}$ and $R_{16}$) and/or ($R_{17}$ and $R_{18}$), together with the nitrogen atom to which they are bonded, form a heterocyclic ring of the formula

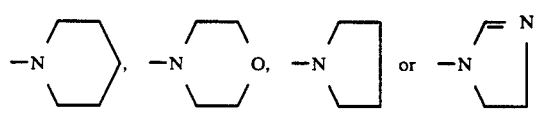

and $A_4$ is $-(CH_2)-_{m_1}$, in which $m_1$ is a number from 1 to 12,

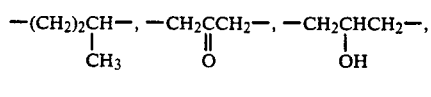

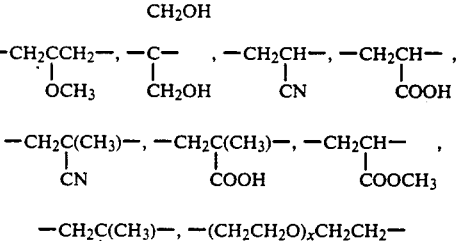

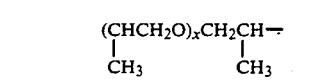

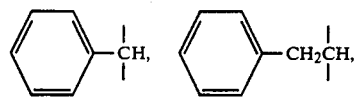

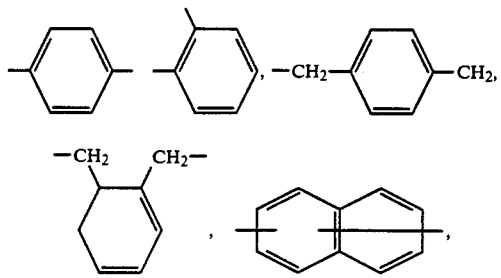

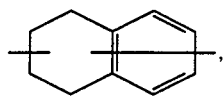

-continued

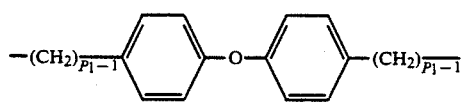

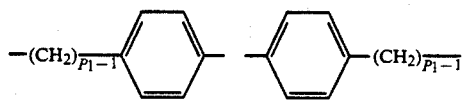

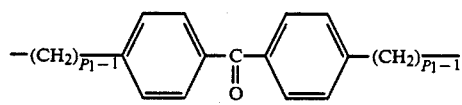

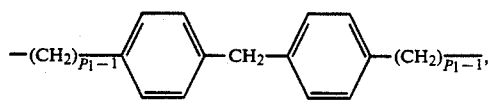

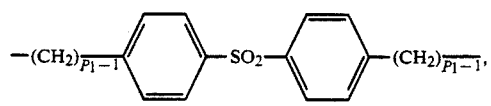

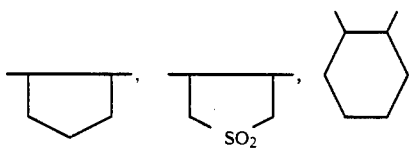

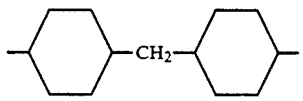

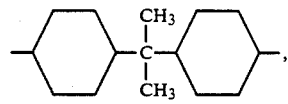

in which x is at least 1 and $P_1$ is 1 or 2, or together with the nitrogen atoms and at least one of the substituents bonded to each nitrogen atom, is a radical of the formula

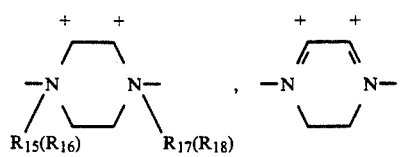

or

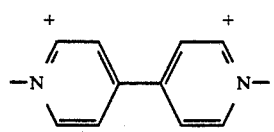

4. The method of claim 1, wherein the recurring units correspond to the formula

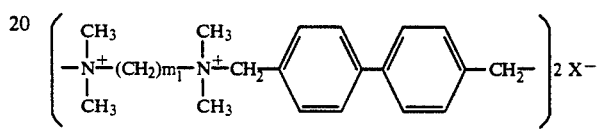

in which
$m_1$ is 1 to 12 and X is halogen.

5. The method of claim 1, wherein the recurring units correspond to the formula

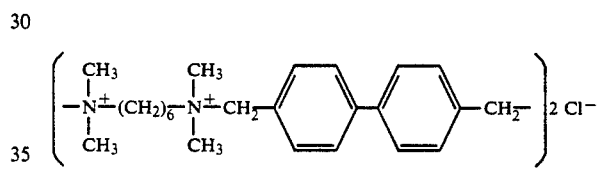

6. The method of claim 1, wherein the quaternary ammonium salt comprises from about 0.0001% to about 3% by weight/volume of the composition.

7. The method of claim 1, wherein said quaternary ammonium salt is used to preserve the composition.

8. The method of claim 7, wherein said quaternary ammonium salt comprises about 0.0005% by weight/volume of the composition.

9. The method of claim 1, wherein said quaternary ammonium salt is used to disinfect an ophthalmic device.

10. The method of claim 9, wherein said quaternary ammonium salt comprises from about 0.001% to 0.005% by weight/volume of the composition.

11. The method of claim 1, wherein said composition is used to disinfect a rigid gas permeable ophthalmic device.

12. The method of claim 11, wherein said rigid gas permeable ophthalmic device is comprises of polymethyl methacrylate.

* * * * *